(12) United States Patent
Toguchi et al.

(10) Patent No.: US 7,722,750 B2
(45) Date of Patent: May 25, 2010

(54) GAS SENSOR WITH IMPROVED HEAT RESISTANCE

(75) Inventors: Kengo Toguchi, Yatomi (JP); Kazuya Nakagawa, Kariya (JP)

(73) Assignee: Denso Corporation, Kariya (JP)

( * ) Notice: Subject to any disclaimer, the term of this patent is extended or adjusted under 35 U.S.C. 154(b) by 618 days.

(21) Appl. No.: 11/698,958

(22) Filed: Jan. 29, 2007

(65) Prior Publication Data

US 2007/0175754 A1 Aug. 2, 2007

(30) Foreign Application Priority Data

Jan. 30, 2006 (JP) .............................. 2006-020354

(51) Int. Cl.
G01N 27/407 (2006.01)
(52) U.S. Cl. ....................... 204/428; 204/424
(58) Field of Classification Search ................. 204/424, 204/428
See application file for complete search history.

(56) References Cited

U.S. PATENT DOCUMENTS

| | | | | |
|---|---|---|---|---|
| 5,785,829 | A | * | 7/1998 | Watanabe .................... 204/427 |
| 5,874,664 | A | * | 2/1999 | Watanabe et al. .......... 73/23.32 |
| 6,623,612 | B2 | | 9/2003 | Shirai |
| 7,318,886 | B2 | | 1/2008 | Nakagawa |
| 2004/0129566 | A1 | | 7/2004 | Nakagawa |

FOREIGN PATENT DOCUMENTS

| | | |
|---|---|---|
| FR | 2 849 200 | 6/2004 |
| JP | 8-160002 | 6/1996 |
| JP | 2002-82085 | 3/2002 |

OTHER PUBLICATIONS

Preliminary Examination Report dated Oct. 27, 2009, issued in corresponding French Application No. 07 00600, with English translation.

* cited by examiner

*Primary Examiner*—Kaj K Olsen
(74) *Attorney, Agent, or Firm*—Nixon & Vanderhye PC (57) ABSTRACT

A gas sensor comprises an atmosphere-side cover, ventilation filter, and filter cover as well as a sensing element and housing. The atmosphere-side cover has i) a first section of a first diameter located on a tip-end side in a axial direction of the housing and fixed on an axially base end of the housing, ii) a second section of a second diameter smaller than the first diameter, the second section being located on an axially base-end side, iii) a stepped section formed between the first and second sections, and iv) a rib protruding outward from the second section and being formed between the stepped section and the second section. The ventilation filter is mounted on the second section and has an axially tip-end section being in contact with an axially base-end section of the rib. The filter cover fixes the ventilation filter between the second section and the filter cover.

16 Claims, 7 Drawing Sheets

GAS SENSOR WITH IMPROVED HEAT RESISTANCE

CROSS-REFERENCE TO RELATED APPLICATION

This application is based on and claims the benefit of priority from earlier Japanese Patent Application No. 2006-020354 filed on Jan. 30, 2006, the description of which is incorporated herein by reference.

BACKGROUND OF THE INVENTION

1. Field of the Invention

The present invention relates to a gas sensor that can be used to control combustion in an internal combustion engine, such as an engine for a vehicle.

2. Description of the Related Art

Conventionally, there is a gas sensor that detects levels of various types of gas components within the exhaust gas.

One example of such gas sensors is shown in Japanese Patent Laid-open Publication No. 2002-82085. In this publication, as shown in FIG. 12, a gas sensor is installed in the exhaust system of an internal combustion engine, such as an engine for a vehicle.

Figure 12:
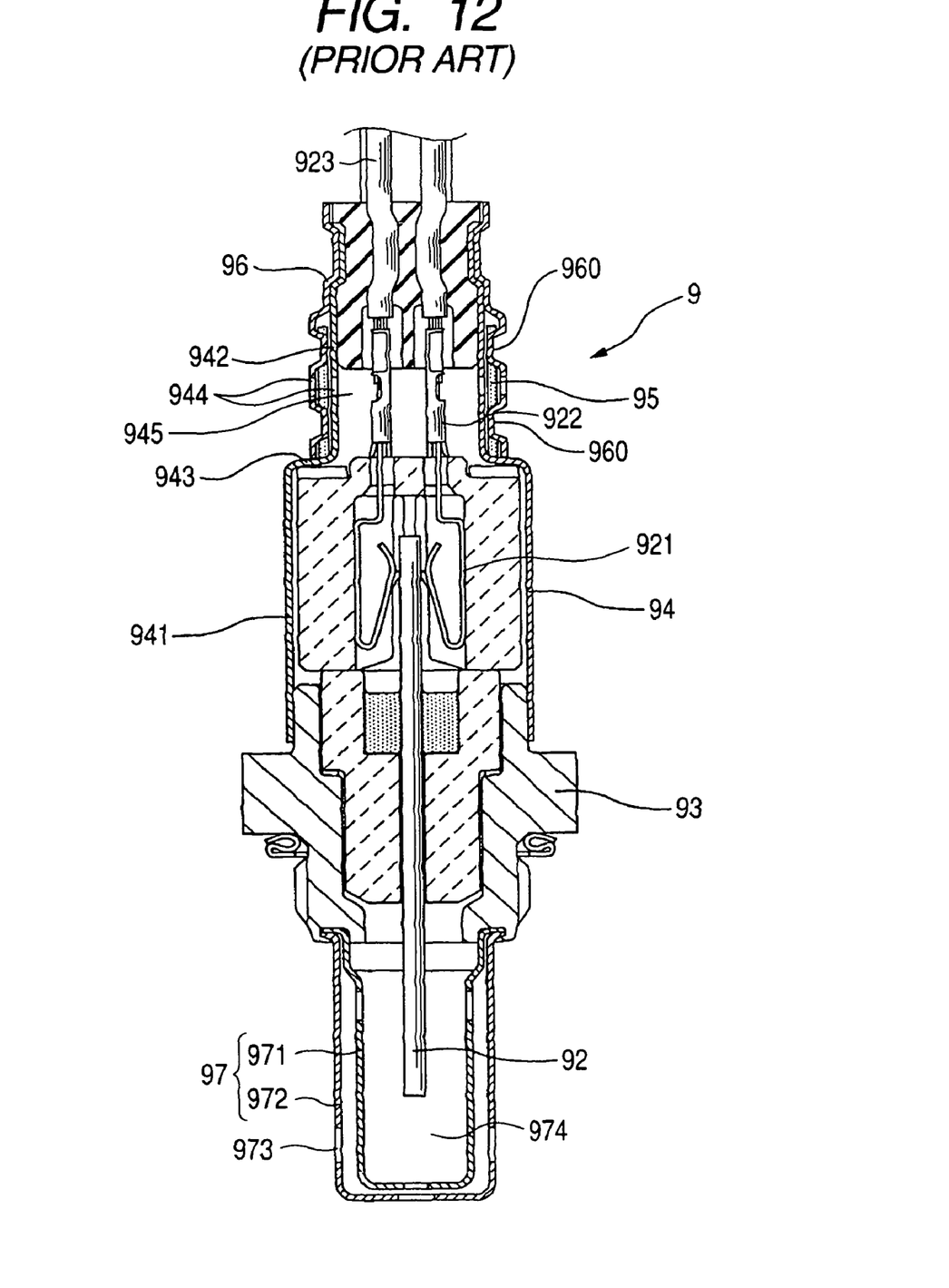
FIG. 12 is a cross-sectional explanatory diagram of a gas sensor according to a conventional example.

Specifically, as shown in FIG. 12, the gas sensor 9 includes a sensing element 92, a housing 93, and an atmosphere-side cover 94. The sensing element 92 detects a particular gas concentration within the gas to be measured. The sensing element 92 is inserted into the housing 93 and held therein. The atmosphere-side cover 94 is fixed onto the base-end side of the housing 93. On the tip-end side of the housing 93, a cover 97 serving as a gas-being-measured-side cover is secured to the housing 93. This cover 97 is formed as a double-structure cover composed of an inner cover 971 and an outer cover 972. Gas introducing openings 973 are formed through both inner and outer covers 971 and 972. Hence, a gas 974 to be measured is introduced into the inside of the inner cover 71 through the openings 973.

As shown in FIG. 12, the atmosphere-side cover 94 includes a large diameter section 941, a small diameter section 942, and a stepped section 943. The large diameter section 941 is fixed onto the housing 93. The small diameter section 942 is mounted on the base-end side of the atmosphere-side cover 94. The stepped section 943 is formed to connect the large diameter section 941 and the small diameter section 942.

The base-end side of the atmosphere-side cover 94 is covered by a filter cover 96. In addition, as shown in the diagram, a waterproof ventilation filter 95 is sandwiched between the atmosphere-side cover 94 and the filter cover 96. The ventilation filter 95 is fastened by fastening sections 960 in a caulking manner, provided in two locations in the axis direction. As shown in FIG. 12, the ventilation filter 95 is positioned so that the tip-end section of the ventilation filter 95 is in contact with the stepped section 943.

Air-introducing openings 944 are formed through both covers 94 and 96, so that atmosphere 945 is introduced into the inside of the atmosphere-side cover 94 through the openings 944. The atmosphere 945 serves as a reference gas.

As is known, the sensing element 92 has the capability of sensing the concentration of a particular (i.e., designated) component of a gas to be measured. A sensed signal from the sensing element 92 is supplied to an external unit via lead portions 921, connectors 922, and lead wires 923.

When the gas sensor 9 is in use, the temperature of the tip-end side of the gas sensor 9 becomes high. The heat is transmitted to the base-end side, and the temperature of the ventilation filter 85 also becomes high. Therefore, the ventilation filter 95 becomes deteriorated by the heat, through repeated use of the gas sensor 9 in the exhaust system of the internal combustion engine. There is risk of the deterioration of the waterproof properties of the ventilation filter 95.

As a result, it is necessary for the ventilation filter 95 to be placed as close to the base end of the gas sensor 9 as possible. Further provision of a new stepped section on the base-end side of the stepped section 943 and disposition of the ventilation filter 95 near the base end of the gas sensor 9 can be considered. However, a narrow crevice is easily formed between the atmosphere-side cover 94 and the filter cover 96 when the stepped section is increased. When moisture or the like leaks into the crevice, it is difficult to drain the moisture or the like. Therefore, there is a risk of crevice corrosion caused by the moisture or the like.

SUMMARY OF THE INVENTION

The present invention has been achieved in light of the foregoing issues. An object of the present invention is to provide a gas sensor that secures ventilation between an atmosphere-side cover and a filter cover and has improved heat-resistance.

The present invention is a gas sensor including a sensing element, a housing, an atmosphere-side cover, a ventilation filter, and a filter cover. The sensing element detects a particular gas concentration within the gas to be measured. The sensing element is inserted into the housing and held therein. The atmosphere-side cover is fixed onto the base-end side of the housing. The ventilation filter is mounted on the outer periphery of the base-end section of the atmosphere-side cover. The filter cover fixes the ventilation filter between the atmosphere-side cover and the filter cover.

In the present invention, the side to be installed within the exhaust pipe of the internal combustion engine of an automobile or the like is described as the tip-end side. The side opposite of the tip-end side is described as the base-end side.

The atmosphere-side cover includes a large-diameter section (i.e., a first section according to the present invention) on the tip-end side and a small-diameter section (i.e., a second section according to the present invention) on the base-end side. The large-diameter section is fixed onto the housing. The filter cover is disposed on the outer periphery of the small-diameter section. A stepped section (i.e., a step-wise section) is formed between the large-diameter section and the small-diameter section.

A rib that protrudes outward from the small-diameter section is formed between the stepped section and the small-diameter section. The tip-end section of the ventilation filter is in contact with the base-end section of the rib.

In this way, the rib is formed between the stepped section and the small-diameter section, and the tip-end section of the ventilation filter is in contact with the base-end section of the rib. Therefore, the ventilation filter can be disposed closer to the base end of the gas sensor by the length of the rib in the axis direction. The ventilation filter can be separated from the tip-end section of the gas sensor that has been heated to a high temperature. As a result, transmission of heat from the tip-end section of the gas sensor to the ventilation filter and heat deterioration of the ventilation filter can be suppressed. A gas sensor having superior heat-resistance can be obtained.

In addition, by the implementation of the above-described configuration, a space that connects to the outside can be formed between the atmosphere-side cover and the tip-end section of the filter cover. Therefore, ventilation between the atmosphere-side cover and the tip-end section of the filter rover can be secured. Thus, corrosion degradation of the ventilation filter, the atmosphere-side cover, and the like can be prevented.

By the tip-end section of the ventilation filter being in contact with the base-end section of the rib, the ventilation filter can be easily positioned and, in addition, disposed at a predetermined position in a stable state.

In this way, according to the present invention, a gas sensor that secures ventilation between an atmosphere-side cover and a filter cover and has superior heat-resistance can be provided.

The length of the rib in the axis direction is preferably 3 to 10 mm. In this case, a gas sensor that prevents the decline in rigidity and strength on the base-end side while having a sufficiently superior heat-resistance can be acquired.

At the same time, when the length in the axis direction is less than 3 mm, it becomes difficult to dispose the ventilation filter so that tip-end section of the gas sensor, which has a high temperature, and the ventilation filter are sufficiently separated. There is also risk of it becoming difficult to prevent the heat-deterioration of the ventilation filter.

In addition, when the length in the axis direction exceeds 10 mm, the measurement of the base-end side of the gas sensor becomes long. There is risk of decline in the rigidity and the strength of the gas sensor on the base-end side.

In addition, three to eight ribs are preferably formed. In this case, the ventilation filter can be disposed with stability, and the ribs can be easily formed.

At the same time, when the number of formed ribs is less than three, there is risk of it becoming difficult for the ventilation filter to be in contact with the base-end section of the rib in a stable state.

In addition, when the number of formed ribs exceeds eight, there is risk of it becoming difficult to form the ribs.

Length A in the circumferential direction of the formation area of the rib and length B in the circumferential direction of the non-formation area between ribs of the atmosphere-side cover preferably have a relationship of $0.15 \leq A/B \leq 1$.

In this case, the ventilation between the atmosphere-side cover and the tip-end section of the filter cover can be sufficiently secured, while positioning the ventilation filter easily and in a stable state.

At the same time, when A/B is less than 0.15, there is a risk that it becomes difficult to position the ventilation filter in a stable state.

In addition, when A/B exceeds 1, the space formed between the atmosphere-side cover and the tip-end section of the filter cover becomes small. There is risk of it becoming difficult to sufficiently secure ventilation between the atmosphere-side cover and the filter cover.

In addition, the tip-end section of the filter cover can be in contact with the base-end section of the rib. In this case, a space than can ventilate to the outside can be formed between the atmosphere-side cover and the tip-end section of the filter cover. Therefore, ventilation between the atmosphere-side cover and the tip-end section of the filter cover can be sufficiently secured.

In addition, the filter cover can be configured to be disposed so that the tip-end section of the filter cover is in contact the outer surface of the rib. In this case, the ventilation filter can be easily positioned in the base-end section of the rib when assembling the gas sensor.

In addition, the filter cover can be disposed so that the tip-end section of the filter cover does not contact the atmosphere-side cover. In this case, a space than can ventilate to the outside can be formed between the atmosphere-side cover and the tip-end section of the filter cover. Therefore, ventilation between the atmosphere-side cover and the tip-end section of the filter cover can be sufficiently secured.

In the present invention, for example, an $O_2$ sensor, an air/fuel (A/F) sensor, an NOx (nitrogen oxides), or a CO (carbon monoxide) sensor is used as the above-described gas sensor.

DETAILED DESCRIPTION OF THE PREFERRED EMBODIMENTS

Referring to the drawings, various embodiments of the gas sensor according to the present invention will now be described.

First Embodiment

The gas sensor according to a first embodiment of the present invention will be described with reference to FIG. 1 to FIG. 3.

Figure 1:
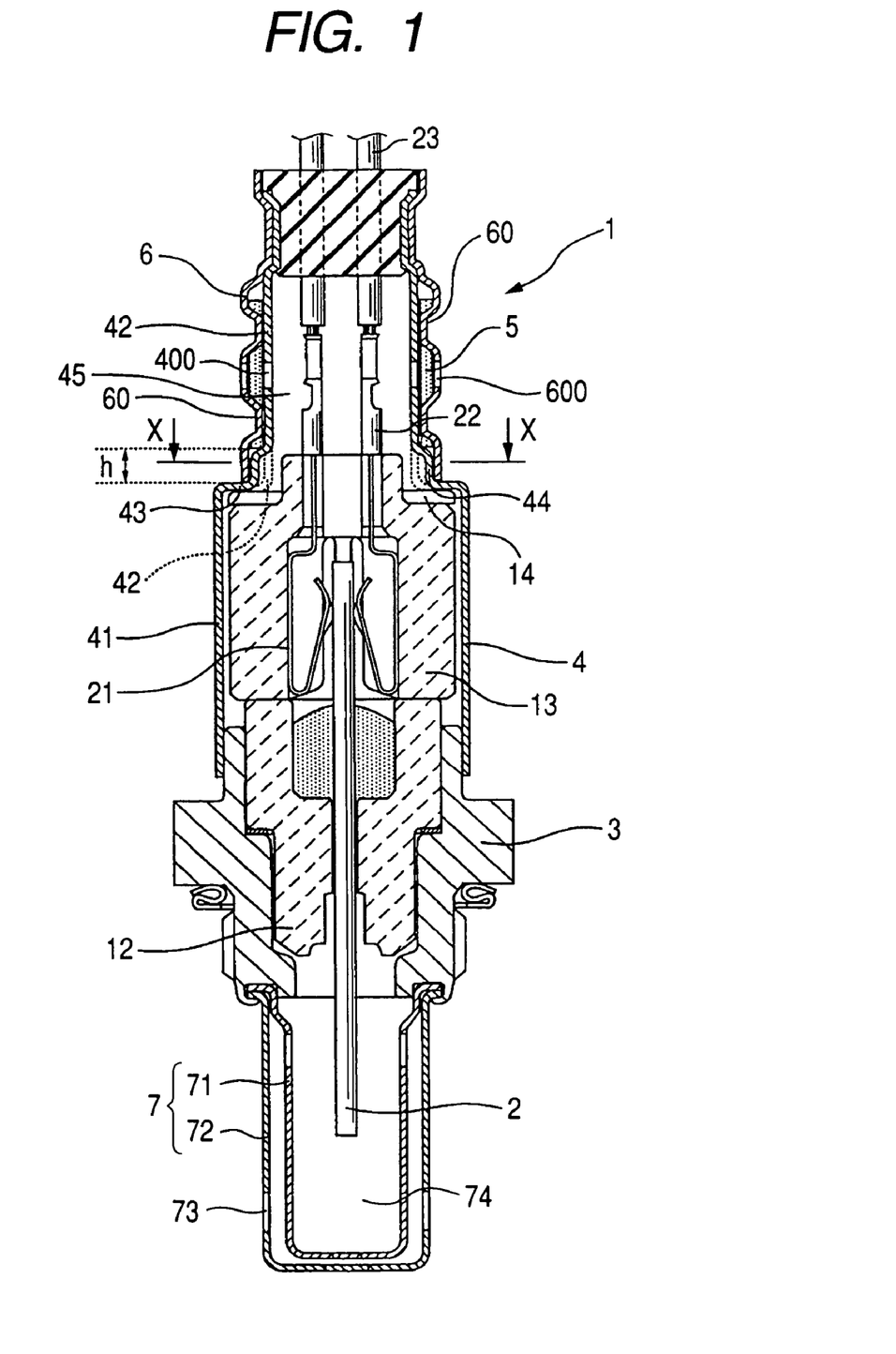
FIG. 1 is a cross-sectional explanatory view of a gas sensor according to a first embodiment of the present invention.

As shown in FIG. 1, a gas sensor 1 according to the present embodiment includes a sensing element 2, a housing 3, an atmosphere-side cover 4, a ventilation filter 5, and a filter cover 6.

In the present embodiment, the sensing element 2 is formed as a tubular member having a length providing an axial direction of the gas sensor 1. In FIG. 1, the lower side is described as a tip-end side to be installed within the exhaust pipe of the internal combustion engine of an automobile or the like, while the upper side is described as a base-end side.

The sensing element 2 detects the concentration of a particular gas within a gas to be measured. The sensing element 2 is inserted inside the housing 3 and held therein. The atmosphere-side cover 4 is fixed onto the base-end side of the housing 3. The ventilation filter 5 is mounted on the outer periphery of the base-end section of the atmosphere-side cover 4. The filter cover 6 fixes the ventilation filter 5 between the atmosphere-side cover 4 and the filter cover 6.

On the tip-end side of the housing 3, a cover 7 serving as a gas-being-measured-side cover is secured to the housing 3. This cover 7 is formed as a double-structure cover composed of an inner cover 71 and an outer cover 72. Gas introducing openings 73 are formed through both inner and outer covers 71 and 72. Hence, a gas 74 to be measured is introduced into the inside of the inner cover 71 through the openings 73.

Figure 3:
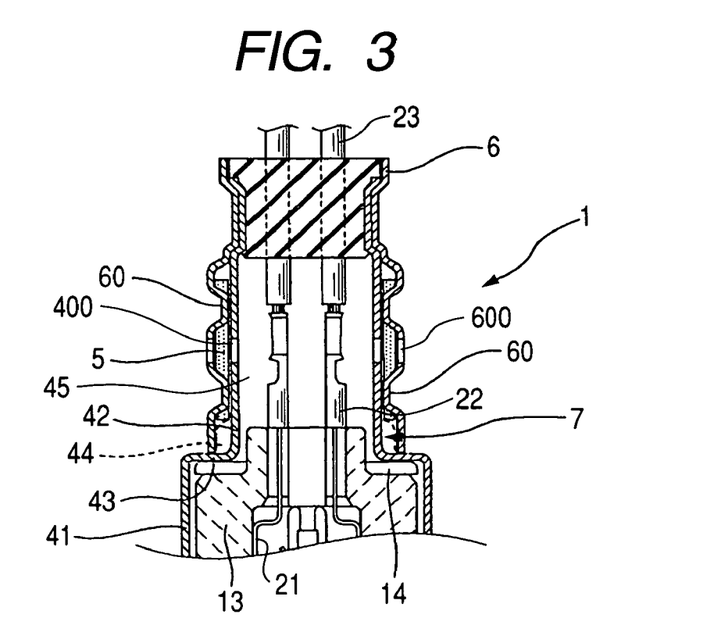
FIG. 3 is a cross-sectional explanatory view taken along line Y-Y in FIG. 2.

As shown in FIG. 1 and FIG. 3, the atmosphere-side cover 4 includes a large-diameter section 41 on the tip-end side and a small-diameter section 42 on the base-end side. The large-diameter section 41 and small-diameter section 42 correspond to a first section and a second section according to the present invention, respectively. The large-diameter section 41 is fixed onto the housing 3. The filter cover 6 is disposed on the outer periphery of the small-diameter section 42. A stepped section 43 is formed between the large-diameter section 41 and the small-diameter section 42.

As shown in FIG. 1 and FIG. 3, a rib 44 that protrudes outward from the small-diameter section 42 is formed between the stepped section 43 and the small-diameter section 42.

The tip-end section of the ventilation filter 5 is in contact with the base-end section of the rib 44.

In addition, the filter cover 6 is disposed so that the tip-end section of the filter cover 6 is in contact with the outer surface of the rib 44.

Figure 2:
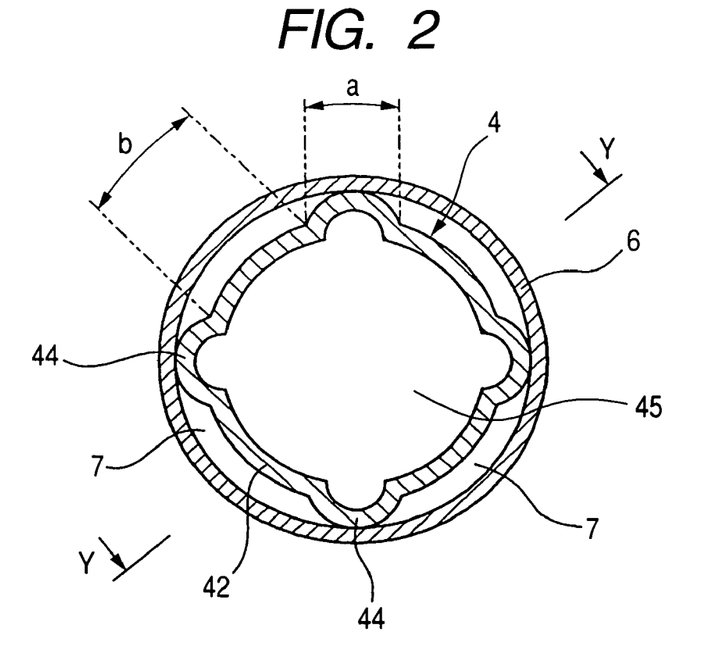
FIG. 2 is a cross-sectional explanatory view taken along line X-X in FIG. 1.

As shown in FIG. 1 and FIG. 2, the above-described rib 44 is formed so as to protrude outward from the small-diameter section 42, between the stepped section 43 and the small-diameter section 42. The length h of the rib 44 in the axis direction is 3 to 10 mm. In the present embodiment, as shown in FIG. 2, four equally-sized, arc-shape ribs 44 are formed equal distances apart, on the small-diameter section 43.

A (=4° a.) is the total of the lengths in the circumferential direction of the four formation areas, when the length in the circumferential direction of the formation area of one rib 44 is "a." B (=4b) is the total of the lengths in the circumferential direction of the four non-formation areas, when the length in the circumferential direction of one non-formation area between the ribs 44 is "b." The dimensions A and B have a relationship of $0.15 \leq A/B \leq 1$. In other words, in the present embodiment, the ribs 44 are formed to be equal in size and equal distances apart. Therefore, the length a in the circumferential direction of the formation area of the rib and the length b in the circumferential direction of the non-formation area between the ribs have a relationship of $0.15 \leq a/b \leq 1$.

After the atmosphere-side cover 4 is formed, the rib 44 can be formed, for example, by the atmosphere-side cover 4 being cast into a mold, and pressed and spread.

As shown in FIG. 1 and FIG. 2, the ventilation filter 5 is sandwiched between the atmosphere-side cover 4 and the filter cover 6. The ventilation filter 5 is fastened and fixed by fastening sections 60 provided in two locations in the axis direction. The ventilation section that is waterproof and introduces air (atmosphere) 45 is formed by an air introduction opening 600, the ventilation filter 5, and an atmosphere communication opening 400. The atmosphere 45 serves as a reference gas. The air introduction opening 600 is provided on the filter cover 6. The atmosphere communication opening 400 is provided on the atmosphere-side filter 4. As the ventilation filter 5, a filter formed from, for example, polytetrafluoroethylene (PTFE) can be used.

The sensing element 2 is known as shown in U.S. Pat. No. 5,573,650 and has the capability of sensing the concentration of a particular (i.e., designated) component of a gas to be measured. For example, the sensing element 2 is a laminated type of heater-incorporated tubular member with two electrodes respectively exposed in the gas 74 to be measured and the atmosphere 45. Ionic current and a potential difference caused between both electrodes provide a sensing signal for measurement of the concentration of a particular gas component of the gas to be measured. The sensing signal from the sensing element 2 is supplied to, for example, an electronic control unit mounted in an automobile, via lead portions 21, connectors 22, and lead wires 23.

In addition, as shown in FIG. 1, the gas sensor 1 includes, within, an element-side electrical porcelain 12, an atmosphere-side electrical porcelain 13, and a Belleville spring 14. The sensing element 2 is inserted into the element-side electrical porcelain 12 and held therein. The atmosphere-side electrical porcelain 13 is disposed on the base-end side of the element-side electrical porcelain 12. The Belleville spring 14 is disposed on the base-end surface of the atmosphere-side electrical porcelain 13. The Belleville spring 14 is disposed between the atmosphere-side electrical porcelain 13 and the stepped section 43 in a state in which the atmosphere-side electrical porcelain 13 is biased to be pressed in the direction of the element-side electrical porcelain 12. The heat of the tip-end section of the gas sensor 1 that has been heated by a high-temperature gas to be measured is transmitted to the Belleville spring 14, via the element-side electrical porcelain 12 and the atmosphere-side electrical porcelain 13. Subsequently, the heat is transmitted from the Belleville spring 14 to the atmosphere-side cover 4 that sandwiches the ventilation filter 5, via the stepped section 43.

Next, the effect of the present embodiment will be described.

As shown in FIG. 1 and FIG. 2, the rib 44 is formed between the stepped section 43 and the small-diameter section 42. The tip-end section of the ventilation filter 5 is in contact with the base-end section of the rib 44. Therefore, the ventilation filter 5 can be disposed closer to the base-end of the gas sensor 1 by the length h of the rib 44 in the axis direction. The ventilation filter 5 can be separated from the tip-end section of the gas sensor 1 that has been heated to a high temperature. As a result, the transmission of the heat from the tip-end section of the gas sensor 1 to the ventilation filter 5 and the heat deterioration of the ventilation filter 5 can be suppressed. A gas sensor 1 having superior heat-resistance can be acquired.

In addition, after the heat of the tip-end section of the gas sensor 1 is transmitted to the Belleville spring 14, as described above, the heat is further transmitted to the atmosphere-side cover 4, via the stepped section 43. Here, through the implementation of the above-described configuration, the area in the stepped section 43 in which the rib 44 is formed is not in contact with the Belleville spring 14. Therefore, the area of the entire stepped section 43 that is in contact with the Belleville spring 14 can be reduced. As a result, the transmission of heat from the tip-end of the gas sensor 1 to the ventilation filter 5 can be suppressed and the heat deterioration of the ventilation filter 5 can be further suppressed.

In addition, through the implementation of the above-described configuration, as shown in FIG. 2 and FIG. 3, a space 7 that connects to the outside can be formed between the atmosphere-side cover 4 and the tip-end section of the filter cover 6. Therefore, ventilation between the atmosphere-side cover 4 and the tip-end section of the filter cover 6 can be secured. Thus, corrosion degradation of the ventilation filter 5, the atmosphere-side cover 4, and the like can be prevented.

By the tip-end section of the ventilation filter 5 being in contact with the base-end section of the rib 44, the ventilation filter 5 can be easily positioned and, in addition, disposed at a predetermined position in a stable state.

As shown in FIG. 1, the length h of the rib 44 in the axis direction is 3 to 10 mm. Therefore, a gas sensor 1 that prevents the decline in rigidity and strength on the base-end side while having a sufficiently superior heat-resistance can be acquired.

In addition, as shown in FIG. 2, four ribs 44 are formed. Therefore, the ventilation filter 5 can be disposed with stability, and the ribs 44 can be easily formed.

In addition, in the atmosphere-side cover 4 according to the present embodiment, the length A in the circumferential direction of the formation area of the rib 44 and the length B in the circumferential direction of the non-formation area between the ribs 44 have a relationship of $0.15 \leq A/B \leq 1$. Therefore, ventilation between the atmosphere-side cover 4 and the tip-end section of the filter cover 6 can be sufficiently secured while positioning the ventilation filter 5 easily and in a stable state.

In addition, as shown in FIG. 1 to FIG. 3, the filter cover 6 is disposed so that the tip-end section of the filter cover 6 is in contact with the outer surface of the rib 44. As a result, the ventilation filter 5 can be easily positioned in the base-end section of the rib 44 when assembling the gas sensor 1.

As described above, according to the present embodiment, a gas sensor that can secure ventilation between the atmosphere-side cover and the filter cover and has superior heat-resistance can be provided.

The configuration of the present invention can be applied not only to the gas sensor 1 having the stacked-type sensing element 2, as in the first embodiment, but also a gas sensor having a cup-shaped sensing element, which is formed into a cylinder with a bottom.

In addition, the ribs 44 are not limited to four ribs as in the first embodiment. The effects of the present invention can be achieved if one or more ribs are formed.

Second Embodiment

Figure 4:
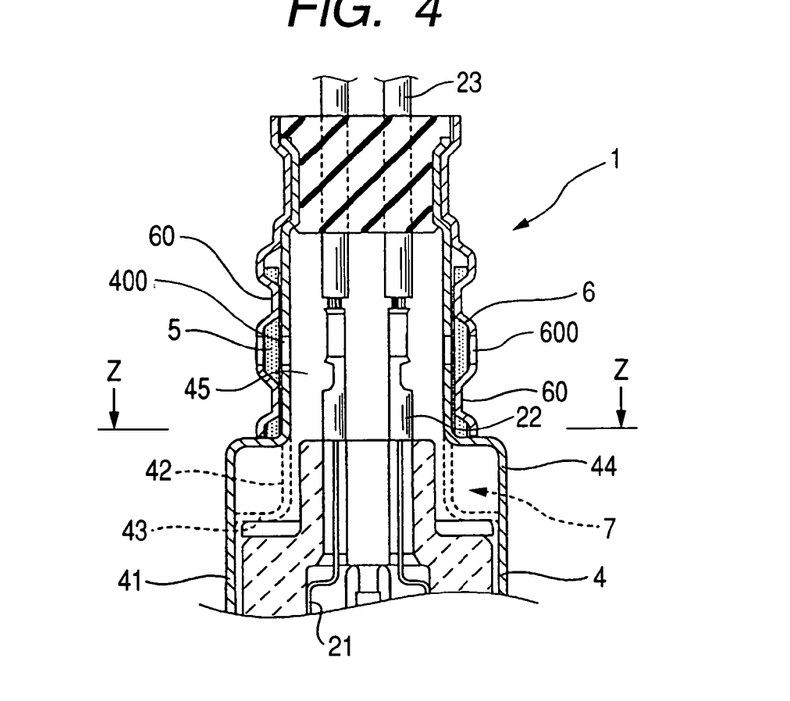
FIG. 4 is a cross-sectional explanatory view of the base-end section of a gas sensor according to a second embodiment of the present invention.
Figure 5:
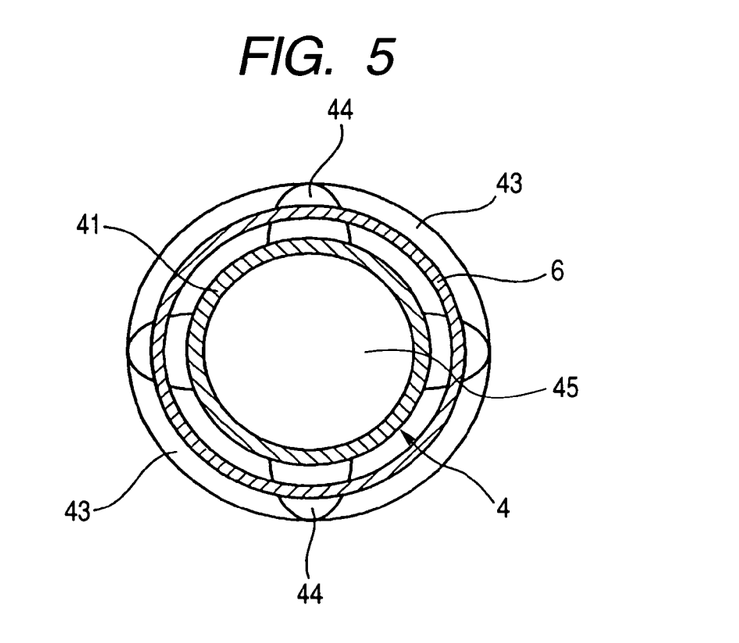
FIG. 5 is a cross-sectional explanatory view taken along line Z-Z in FIG. 4.

Referring to FIGS. 4 and 5, a second embodiment of the present invention will now be described. In the second and subsequent embodiments, the similar or identical components to those in the first embodiment are given the same reference numerals for the sake of a simplified explanation.

As shown in FIG. 4 and FIG. 5, there is provided a gas sensor 1 according to a second embodiment, in which the tip-end section of the filter cover 6 is in contact with the base-end section of the rib 44.

The rib 44 is formed to protrude farther than the ribs in the first embodiment (refer to reference number 44 in FIG. 1 and FIG. 2), in the base-end side direction of the axis direction and the outside-direction of the circumferential direction. In the present embodiment, the outer surface of the ribs 44 in the circumferential direction and the outer periphery surface of the large-diameter section 41 have the same amount of protrusion in the circumferential direction.

This embodiment is otherwise the same as the first embodiment.

In the present embodiment, the space 7 that can allow ventilation with the outside can be formed between the atmosphere-side cover 4 and the tip-end section of the filter cover 6. Therefore, ventilation between the atmosphere-side cover 4 and the tip-end section of the filter cover 6 can be sufficiently secured.

The effects of this embodiment are otherwise the same as those of the first embodiment.

Third Embodiment

Figure 6:
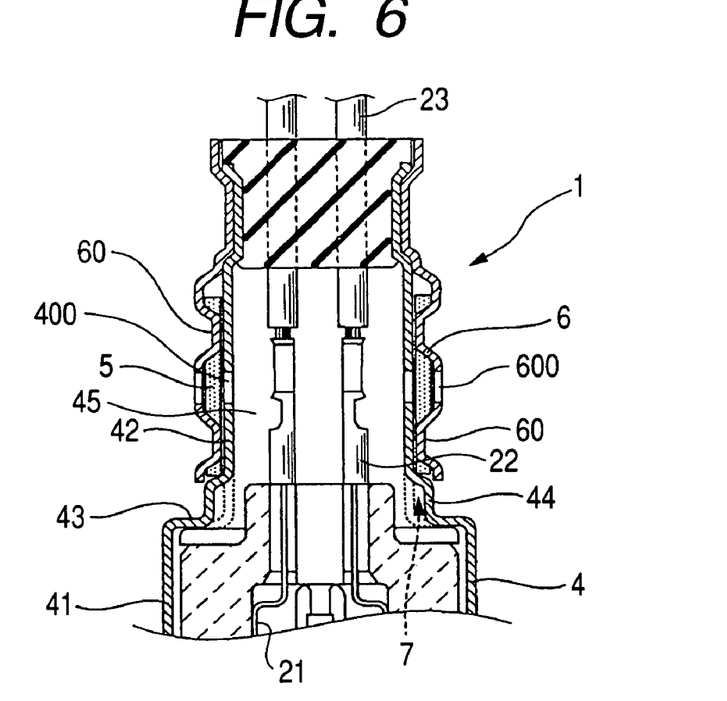
FIG. 6 is a cross-sectional explanatory view of the base-end section of a gas sensor according to a third embodiment of the present invention.

Referring to FIG. 6, a third embodiment of the present invention will now be described.

As shown in FIG. 6, there is provided a gas sensor 1 according to a third embodiment, in which the filter cover 6 is disposed so that the tip-end section of the filter cover 6 does not contact the atmosphere-side cover 4

This embodiment is otherwise the same as the first embodiment.

In the present embodiment, the space 7 that can allow ventilation with the outside can be formed between the atmosphere-side cover 4 and the tip-end section of the filter cover 6. Therefore, ventilation between the atmosphere-side cover 4 and the filter cover 6 can be sufficiently secured.

The effects of this embodiment are otherwise the same as those of the first embodiment.

Fourth Embodiment

Figure 7:
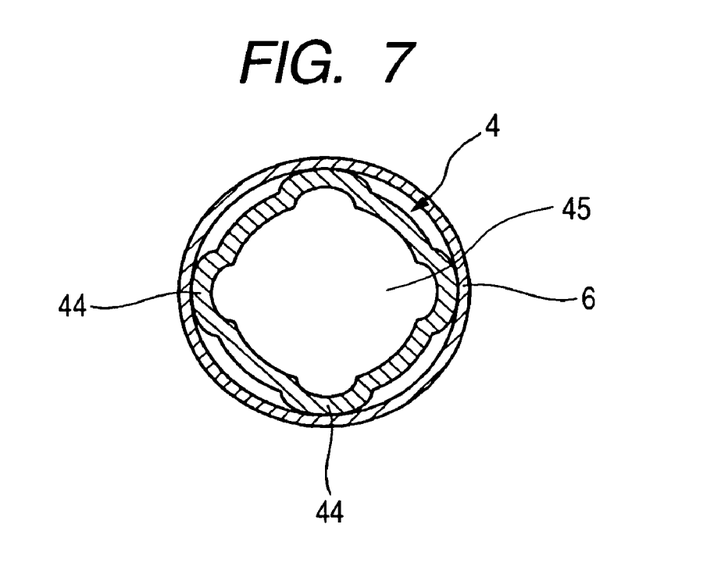
FIG. 7 is a cross-sectional explanatory view of the atmosphere-side cover in a direction perpendicular to the axis direction when the cross-sectional shape of the rib is changed in a fourth embodiment of the present invention.
Figure 8:
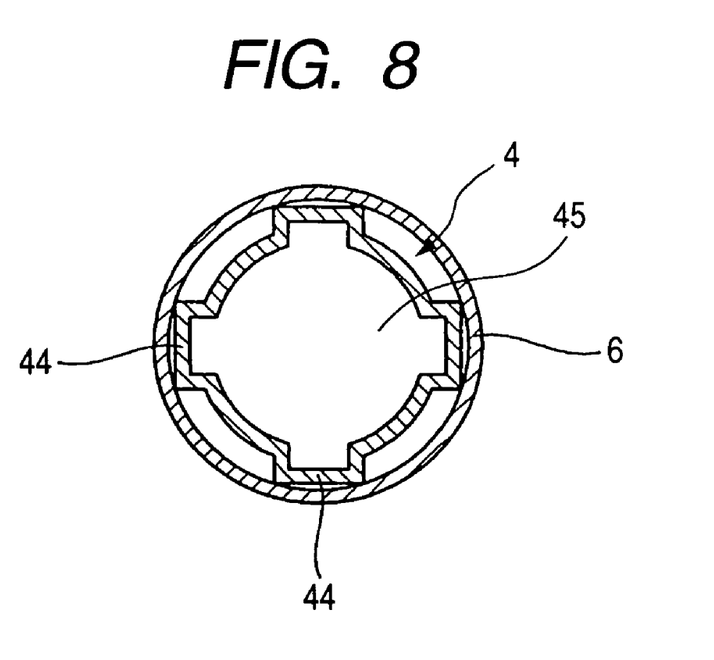
FIG. 8 is a cross-sectional explanatory view of the atmosphere-side cover in the direction perpendicular to the axis direction when the cross-sectional shape of the rib is changed in the fourth embodiment.
Figure 9:
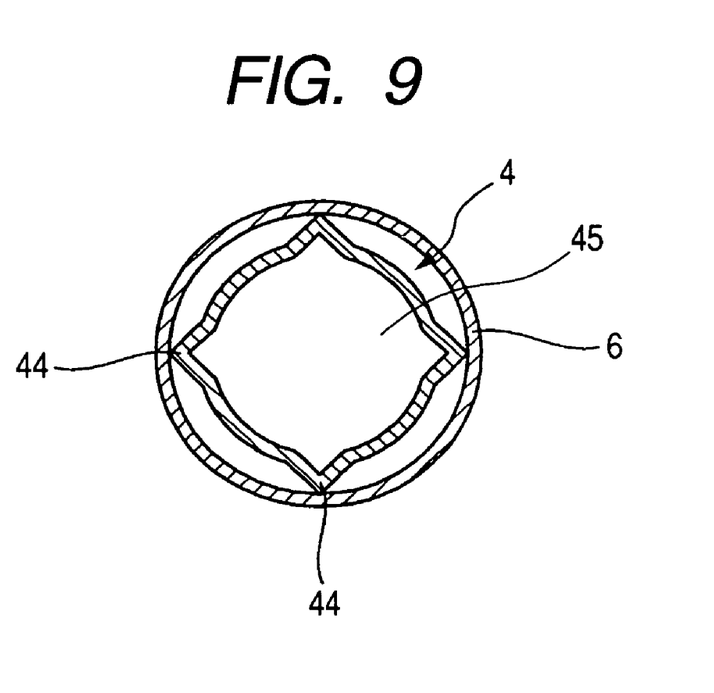
FIG. 9 is a cross-sectional explanatory view of the atmosphere-side cover in the direction perpendicular to the axis direction when the cross-sectional shape of the rib is changed in the fourth embodiment.

Referring to FIGS. 7 to 9, a fourth embodiment of the present invention will now be described.

As shown in FIG. 7 to FIG. 9, a gas sensor 1 according to a fourth embodiment relates to the atmosphere-side cover 4 including the rib 44 of which the cross-section in the direction perpendicular in the axis direction is variably changed. In other words, the cross-section of the rib 44 can be elliptical as shown in FIG. 7, rectangular as shown in FIG. 8, or triangular as shown in FIG. 9.

The configuration and the effects of this embodiment are otherwise the same as those of the first embodiment.

Fifth Embodiment

Figure 10:
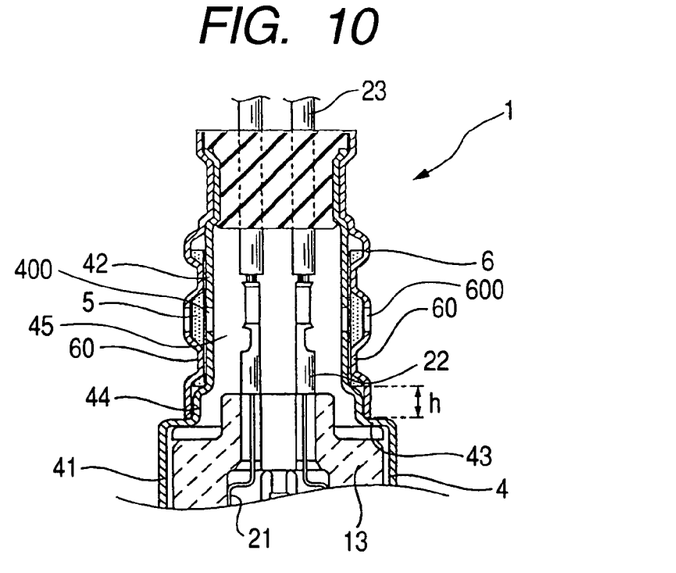
FIG. 10 is a cross-sectional explanatory diagram of the base-end section of a gas sensor according to a fifth embodiment of the present invention.
Figure 11:
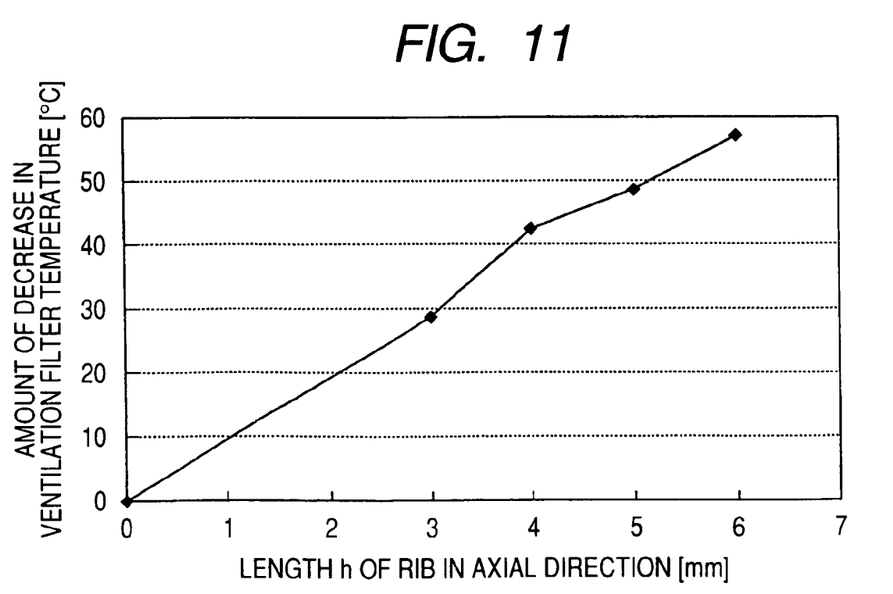
FIG. 11 is a line graph showing the measurement results according to the fifth embodiment.

Referring to FIGS. 10 and 11, a fifth embodiment of the present invention will now be described.

As shown in FIG. 10 and FIG. 11, in a fifth embodiment, the length h of the rib 44 in the axis direction is variably changed and the amount of decrease in the temperature of the ventilation filter 5 is studied.

The amount of decrease in the temperature is the difference between the temperature of the ventilation filter in the conventional gas sensor (refer to the reference number 9 in FIG. 12) in which the length h in the axis direction is 0 and the temperature of the ventilation filter 5 in the gas sensor 1 when the length h in the axis direction is variably changed, as shown in FIG. 10. The amount of decrease in the temperature is measured under conditions for actual use of the gas sensor.

The measurement results of the decrease amount in the temperature are shown in FIG. 11. As can be seen from the diagram, it is clear that the amount of decrease in the temperature of the ventilation filter 5 becomes larger by the length of the rib 44 in the axis direction 44 being increased. In other words, as the position of the tip-end section of the ventilation filter 5 is moved to the base-end side, it is clear that the transmission of heat from the tip-end section of the gas sensor 1 to the ventilation filter 5 can be suppressed. Furthermore, when the length h in the axis direction is 3 mm or more, the amount of decrease in temperature is 28° C. or more. The effects of the present invention can be sufficiently achieved.

The present invention may be embodied in several other forms without departing from the spirit thereof. The embodiments and modifications described so far are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A gas sensor comprising:

a sensing element that detects a concentration of a particular gas component within a gas to be measured and outputs an electric signal corresponding to the detected concentration;

a housing in which the sensing element is inserted and held, the sensing element held in the housing having a length direction defining an axial direction of the housing, the housing having both a radial direction perpendicular to the axial direction and a circumferential direction encircling the axial direction, the housing having a base end and a tip end both located along the axial direction;

an atmosphere-side cover formed as an approximately cylindrical member having i) a first section of a first diameter which is located on a tip-end side in the axial direction and which is fixed on the base end of the housing, ii) a second section of a second diameter smaller than the first diameter, the second section being located on a base-end side in the axial direction and having an outer periphery, iii) a stepped section formed between the first and second sections to connect both the first and second sections with each other, and iv) a plurality of ribs each protruding outward in the radial direction from an axial end portion of the second section so that the plurality of ribs are located next to the stepped section in the axial direction and spaced apart from one another in the circumferential direction, each rib having a base-end section in the axial direction;

a ventilation filter mounted on the outer periphery of the second section and formed to have a tip-end section in the axial direction, the tip-end section of the ventilation filter being in contact with the base-end section of the ribs; and a filter cover that covers the ventilation filter so that the ventilation filter is fixedly placed between the second section of the atmosphere-side cover and the filter cover, the filter cover having a tip-end section in the axial direction, the tip-end section being in contact with the ribs so that a space is defined by the second section of the atmosphere-side cover, adjacent two ribs of the ribs, and the filter cover, the space communicating with an outside of the gas sensor, wherein a circumferential length A of a rib-formation area of the second section that is protruded to form each rib and a circumferential length B of a non-ribbed area of the second section that is between adjacent two ribs have the relationship:

$0.15 \leq A/B \leq 1$.

2. The gas sensor according to claim 1, wherein a length of each of the ribs in the axial direction is 3 to 10 mm.

3. The gas sensor according to claim 2, wherein said plurality of ribs comprises at least three and no more than eight ribs.

4. The gas sensor according to claim 3, wherein the tip-end section of the filter cover is in contact with the base-end section of each of the ribs.

5. The gas sensor according to claim 3, wherein the tip-end section of the filter cover is in contact with radial outer surfaces of the ribs.

6. The gas sensor according to claim 3, wherein the tip-end section of the filter cover is spaced apart from the atmosphere-side cover.

7. The gas sensor according to claim 2, wherein the tip-end section of the filter cover is in contact with the base-end section of each of the ribs.

8. The gas sensor according to claim 2, wherein the tip-end section of the filter cover is in contact with radial outer surfaces of the ribs.

9. The gas sensor according to claim 2, wherein the tip-end section of the filter cover is spaced apart from the atmosphere-side cover.

10. The gas sensor according to claim 1, wherein said plurality of ribs comprises at least three and no more than eight ribs.

11. The gas sensor according to claim 8, wherein the tip-end section of the filter cover is in contact with the base-end section of each of the ribs.

12. The gas sensor according to claim 10, wherein the tip-end section of the filter cover is in contact with radial outer surfaces of the ribs.

13. The gas sensor according to claim 10, wherein the tip-end section of the filter cover is spaced apart from the atmosphere-side cover.

14. The gas sensor according to claim 1, wherein the tip-end section of the filter cover is in contact with the base-end section of each of the ribs.

15. The gas sensor according to claim 1, wherein the tip-end section of the filter cover is in contact with radial outer surfaces of the ribs.

16. The gas sensor according to claim 1, wherein the tip-end section of the filter cover is spaced apart from the atmosphere-side cover.

* * * * *

UNITED STATES PATENT AND TRADEMARK OFFICE
CERTIFICATE OF CORRECTION

PATENT NO. : 7,722,750 B2 Page 1 of 1
APPLICATION NO. : 11/698958
DATED : May 25, 2010
INVENTOR(S) : Toguchi et al.

It is certified that error appears in the above-identified patent and that said Letters Patent is hereby corrected as shown below:

At column 10, line 34, "claim 8" should be --claim 10--

Signed and Sealed this

Thirteenth Day of July, 2010

David J. Kappos
*Director of the United States Patent and Trademark Office*